United States Patent
Borczuch-Laczka et al.

(10) Patent No.: US 9,260,342 B2
(45) Date of Patent: Feb. 16, 2016

(54) PROCESS FOR PREPARING A GLASS-CERAMIC BODY

(75) Inventors: Maria Borczuch-Laczka, Krakow (PL); Katharzyna Cholewa-Kowalska, Krakow (PL); Karolina Laczka, Krakow (PL)

(73) Assignee: STRAUMANN HOLDING AG, Basel (CH)

( * ) Notice: Subject to any disclaimer, the term of this patent is extended or adjusted under 35 U.S.C. 154(b) by 0 days.

(21) Appl. No.: 14/111,924

(22) PCT Filed: Apr. 20, 2012

(86) PCT No.: PCT/EP2012/001709
§ 371 (c)(1),
(2), (4) Date: Jan. 26, 2014

(87) PCT Pub. No.: WO2012/143137
PCT Pub. Date: Oct. 26, 2012

(65) Prior Publication Data
US 2014/0141960 A1    May 22, 2014

(30) Foreign Application Priority Data
Apr. 20, 2011 (EP) ................................. 11003315

(51) Int. Cl.
*C03C 10/14* (2006.01)
*C03C 10/00* (2006.01)
(Continued)

(52) U.S. Cl.
CPC ............. *C03C 10/0027* (2013.01); *A61K 6/024* (2013.01); *A61K 6/025* (2013.01);
(Continued)

(58) Field of Classification Search
CPC ............ C03C 10/0027; C03C 10/0045; C03C 10/0009; C03C 3/093; C03C 3/083; C03C 3/087
USPC ............................................. 501/4, 5, 6, 7, 68
See application file for complete search history.

(56) References Cited

U.S. PATENT DOCUMENTS 2,971,853 A * 2/1961 Stookey ............................. 501/4
3,464,807 A   9/1969 Pressau
(Continued)

FOREIGN PATENT DOCUMENTS

CN   1684918A A   10/2005
DE   19750794       6/1999
(Continued)

OTHER PUBLICATIONS

International Search Report in PCT/EP2012/001709.
(Continued)

*Primary Examiner* — Noah Wiese
(74) *Attorney, Agent, or Firm* — Oliff PLC

(57) ABSTRACT

Process for preparing glass-ceramic body including the steps of providing a basic glass body and subjecting the basic glass body to a thermal treatment whereby a crystalline phase embedded in a glass matrix is formed. The basic glass body is made of a composition comprising 65 to 72 wt-% $SiO_2$, at least 10.1 wt-% $Li_2O$ and at least 10.1 wt-% $Al_2O_3$ based on the total weight of the composition, the proportion of $Li_2O$ to $Al_2O_3$ being from 1:1 to 1.5:1. The thermal treatment involves a nucleation step followed by several crystallization steps at different temperatures, whereby at least two different crystalline phases are formed.

11 Claims, 2 Drawing Sheets

(51) Int. Cl.
*A61K 6/02* (2006.01)
*A61K 6/027* (2006.01)
*C03C 3/083* (2006.01)
*C03C 4/00* (2006.01)
*C03C 23/00* (2006.01)
*C03C 3/097* (2006.01)

(52) U.S. Cl.
CPC ............ *A61K 6/0235* (2013.01); *A61K 6/0255* (2013.01); *A61K 6/0273* (2013.01); *C03C 3/083* (2013.01); *C03C 3/097* (2013.01); *C03C 4/0021* (2013.01); *C03C 23/0005* (2013.01); *C03C 23/0025* (2013.01)

(56) References Cited

U.S. PATENT DOCUMENTS

| | | | |
|---|---|---|---|
| 5,939,211 | A | 8/1999 | Mormann |
| 6,284,340 | B1 | 9/2001 | Abe et al. |
| 6,376,084 | B1 * | 4/2002 | Kishimoto et al. ........... 428/426 |
| 6,420,288 | B2 | 7/2002 | Schweiger et al. |
| 6,514,890 | B1 * | 2/2003 | Nagata et al. ..................... 501/4 |
| 7,452,835 | B2 | 11/2008 | Bridges et al. |
| 7,452,836 | B2 | 11/2008 | Apel et al. |
| 2002/0010063 | A1 | 1/2002 | Schweiger et al. |
| 2008/0213727 | A1 | 9/2008 | Zhang et al. |
| 2011/0030423 | A1 | 2/2011 | Johannes et al. |

FOREIGN PATENT DOCUMENTS

| | | |
|---|---|---|
| DE | 102007011337 | 9/2008 |
| JP | H06-279054 A | 10/1994 |
| WO | WO0034196 | 6/2000 |
| WO | 2004/031089 A1 | 4/2004 |
| WO | WO2010/010082 | 1/2010 |

OTHER PUBLICATIONS

Fujiwara, et al., "Laser induced photonic periodic structure in tellurite based glass ceramics", Physics and Chemistry of Glasses vol. 43C 2002, pp. 213-215.

Gupta, et al., "Creation of tailored features by laser heating of Nd0.2La0.8BGeO5glass" P. Gupta, et al., Optical Materials 2005, pp. 1-5.

Honma, et al., "Technique for writing of nonlinear optical single-crystal lines in glass", Applied Physics Letters, 2003 vol. 83, No. 14, pp. 2796-2798.

Kawasaki et al., "Writing of crystal-dots and lines by YAG laser irradiation and their morphologies in samarium tellurite glasses", Journal of Non-Crystalline Solids 325 (2003), pp. 61-69.

Dec. 3, 2015 Communication issued in European Application No. 12717603.0.

D.U. Tulyaganov et al., "Synthesis and properties of lithium disilicate glass-ceramics in the system $SiO_2-Al_2O_3-K_2O-Li_2O$," Science Direct, Ceramics International 35 (2009) 3013-3019.

O.R.K. Montedo et al., "Lithium-Zirconium-Silicon glass-ceramic system's high coefficient of thermal expansion makes it inadequate for many applications, but the coefficient can be lowered by the addition of alumina," American Ceramic Society Bulletin, vol. 87, No. 7, 34-40 (2008).

* cited by examiner

PROCESS FOR PREPARING A GLASS-CERAMIC BODY

FIELD OF THE INVENTION

The present invention relates to a process for preparing a glass-ceramic body, to a glass composition for said process, as well as to a glass-ceramic body obtainable by said process and to the use of said glass-ceramic body for a dental restoration.

BACKGROUND

Glass-ceramic materials comprise an amorphous (glass) phase and one or more crystalline (ceramic) phases embedded in the amorphous phase. Due to the presence of both an amorphous and a crystalline phase, glass-ceramics share many properties with both glasses and ceramics. They are used in a variety of different technical fields, for example as cooktops, cookware and bakeware, as a substrate for magnetic disks or as high performance reflectors for digital projectors.

Glass-ceramics are of particular interest in the field of restorative dentistry, in which the need for prostheses that, in terms of functionality and appearance, would perform exactly like their natural counterparts has been expressed.

Conventionally, dental restorations have been prepared according to the "porcelain fused to metal" (PFM) method in which the supporting metal framework is used in conjunction with a veneering layer of a ceramic material which makes up the colour of the prosthesis. The preparation of restorations according to this method implies many manufacturing steps and is hence laborious.

The PFM method has been developed further by replacing the metallic framework by a non-metallic inorganic framework. In this regard, a feldspathic glass filled with alumina particles has been proposed. Further development has led to substituting an opaque ceramic framework for the alumina-reinforced glass.

Dental crowns and bridges are today mostly manufactured by CAD/CAM technologies, which are increasingly gaining importance. The fabrication process comprises two decisive stages: a computer-aided design of the restoration and its computer-aided milling. In the stage of milling, the restoration is machined out of a blank.

DE-A-19750794 has proposed a process for preparing a lithium disilicate glass product suitable for the use as a dental product. The process is aiming at a high chemical stability, a high translucency and good mechanical properties of the product. Due to the high strength and toughness obtained, the machining of the material results, however, in a very high wear of the machining tools and very long processing times. Furthermore, restorations prepared according to this technique show only a poor strength when their thickness falls within a range of only a few hundreds of micrometers.

U.S. Pat. No. 7,452,836 relates to a process for providing a glass-ceramic which has metastable lithium metasilicate ($Li_2SiO_3$) as main crystalline phase. This lithium metasilicate glass-ceramic has mechanical properties allowing it to be easily machined into the shape of even complicated dental restorations without undue wear of tools. It can be converted by further heat treatment into a lithium disilicate glass-ceramic with very good mechanical properties and translucency.

Although U.S. Pat. No. 7,452,836 allows for achieving materials having a flexural strength which might be sufficient for the restoration of multiple missing teeth in the front (for example 3-unit bridges), its strength is still not sufficient for posterior bridges or large restorations.

Aiming not only at an improvement in mechanical properties, but also at a highly aesthetical appearance, a material having an internal structure mimicking the structure of a natural tooth would be highly appreciated.

Natural teeth consist of a hard, inert and acellular enamel supported by the less mineralized, more resilient and vital hard tissue dentin. Because of its exceptionally high mineral content, enamel is a brittle tissue unable to withstand the forces of mastication without fracture unless it has the support of the more resilient dentin.

Enamel and dentin do not only differ in their mechanical properties, namely their compressive strength, elastic modulus and coefficient of thermal expansion, but also in their appearance. Whereas enamel is translucent and varies in colour from light yellow to gray-white, dentin is yellow. In a natural tooth, the thickness of enamel varies from a maximum of approximately 2.5 mm to a fraction thereof. This variation influences the tooth's appearance because the underlying dentin is seen through the thinner enamel region, whereas it gradually fades out towards thicker ones.

In summary, a natural tooth has thus an inhomogeneous structure different than in the glass-ceramic of U.S. Pat. No. 7,452,835, in which crystals are grown throughout the whole volume without any spatial order. In contrast to a natural tooth, which exhibits a different composition and structure in different parts, be it in the dentin or the enamel part, a restoration made of the material according to U.S. Pat. No. 7,452,835 is with respect to the material constitution rather homogeneous and does not comprise regions of different constitutions like the natural counterpart does. A natural tooth can thus not be mimicked perfectly by the material according to U.S. Pat. No. 7,452,835.

Biocompatible, highly aesthetical and robust materials with an internal structure mimicking that of a natural tooth for a single tooth replacement (crowns) and for a prosthesis formed by two or more crowns (bridges) supported by modified natural teeth are, however, of paramount importance in the field of restorative dentistry. Further, as more dental laboratories adopt CAD/CAM devices, laboratory-generated CAD/CAM prostheses are expected to rise significantly in the decades ahead. This evolution poses an additional requirement to materials for the fabrication of restoration viz. CAD/CAM machining at affordable costs.

A method for manufacturing prostheses from a blank comprising at least one layer of high abrasive resistance, at least one layer of high flexural strength and at least one layer of lower hardness and strength is disclosed in U.S. Pat. No. 5,939,211. During the milling of the restoration, material removal is performed in such a manner that layers with high strength constitute a reinforcing structure.

Based on the finding that a so-called functionally graded material can lead to an improved resistance in contact damages, US 2008/0213727 proposes a process for providing a functionally graded material including infiltrating top and bottom ceramic surfaces with glass. The resulting structure comprises an outer (aesthetic) surface residual glass layer, a graded glass-ceramic layer and a dense interior ceramic.

Further, WO 2010/010082 aims at a material mimicking the colour gradients in a natural tooth and relates to a form-stabilized material comprising a first component and a second component, the second component having a different pigmentation than the first component and being disposed in the first component such that the boundary surface between the components represents a spatially curved surface.

In particular regarding U.S. Pat. No. 5,939,211 and WO 2010/010082, the presence of physically distinct component layers and thus of an interface between different components can have an impact on the overall stability of the dental restoration. Also, the processes according to these documents are relatively laborious.

The technique according to US 2008/0213727 allows a gradient of only a very small thickness to be formed. In addition, the gradient is confined to the surface area of the material; the formation of a gradient within the bulk of the material remote from the surface is however not possible according to US 2008/0213727.

SUMMARY OF THE INVENTION

In general, it would be highly desirable to provide a glass-ceramic body, the properties of which can be adjusted to the actual need in a simple and straightforward manner.

In particular for achieving dental restorations, with both high aesthetics and superior mechanical properties, a glass-ceramic body would be desirable for which different mechanical and optical properties can be obtained at different regions of one and the same body.

More particularly and in view of the drawbacks of US 2008/0213727, a glass-ceramic body would be desirable comprising different crystalline phases changing from one region to another in a gradual manner and not being locally limited to specific areas of the material, thus being able to mimic the structure of a natural tooth.

The object of the present invention is thus to provide such a glass-ceramic body in a simple and straightforward manner.

According to first aspect, the present invention relates to a process for preparing a glass-ceramic body comprising the steps of providing a basic glass body and subjecting the basic glass body to a thermal treatment whereby a crystalline phase embedded in a glass matrix is formed.

According to the process of the invention, the basic glass body is made of a composition comprising 65 to 72 wt-% $SiO_2$, at least 10.1 wt-% $Li_2O$ and at least 10.1 wt-% $Al_2O_3$ based on the total weight of the composition. Preferably, the proportion of $Li_2O$ to $Al_2O_3$ is at least 1:1, more preferably about 3:2.

According to a specific embodiment, the proportion of $Li_2O$ to $Al_2O_3$ is from 1:1 to 1.5:1.

The thermal treatment involves a nucleation step followed by a first crystallization step at a first temperature range and a second crystallization step at a second temperature range different from the first temperature range. Thereby, at least two crystalline phases different from each other are formed.

It has surprisingly been found that by thermally treating a glass body according to the present invention, not only different crystalline phases can be formed, but that the type of the crystalline phases as well as their proportion can be controlled and thus adjusted to the actual need.

In particular, different crystalline phases can be formed individually or together by applying the required heating for the crystallization steps in a focused manner. Thus, different crystalline phases can be formed in different regions of one and the same body.

Consequently, the present invention allows for achieving a structured glass-ceramic body, i.e. a glass-ceramic body having crystalline phases differing from region to region. In this regard, the present invention further allows different crystalline phases to be achieved changing from one region to another in a gradual manner. This has important implications in particular regarding the mechanical and optical characteristics of the glass-ceramic body, more particularly in view of a use of the body for a dental restoration, as will be discussed in detail below.

As mentioned, the thermal treatment according to the process of the invention comprises a nucleation step prior to the crystallization steps. By the nucleation step, crystallization nuclei are formed. For the nucleation step, the basic glass body, i.e. the "starting glass", is heated to a temperature of 500° C. to 570° C., which is slightly above the glass transition temperature, and a dwell of up to 3 hours is observed. After this treatment, the nucleated glass does not show any significant difference in appearance from the starting glass. Following the nucleation step, the nucleated glass body is heated to higher temperatures and again dwells are observed at specific temperatures (crystallization steps). This treatment leads to differences in both the mechanical properties and appearance of the glass body.

In summary, the process of the present invention, thus, comprises a nucleation step at a first temperature range, after which no significant difference in mechanical properties and appearance from the basic glass body is observed, followed by at least two crystallization steps, each at a temperature range higher than the one of the nucleation step, said crystallization steps leading to the formation of at least two different crystalline phases and, thus, to a glass-ceramic body having mechanical properties and an appearance different from the one of the basic glass body.

The crystallization steps, thus, differ from the nucleation step in that they are performed at higher temperatures and that they go along with a change in both the mechanical properties and appearance of the material.

The thermal treatment of the present invention involving two crystallization steps is different from the one described in DE 10 2007 011 337 relating to veneer ceramics for dental restorations, the process of the latter comprising merely one crystallization step. The same applies to WO 00/34196, which relates to glass-ceramics useful in the fabrication of single and multi-unit dental restorations and which describes a process of manufacture comprising merely one crystal growth step after a nucleation step. Also, U.S. Pat. No. 6,514, 890 describes a process comprising a single crystallization step after a nucleation step, said document being—irrespective of the fact that a different glass composition is used—thus different from the present invention.

Specifically, the basic glass body is heated to a temperature in the range from 500° C. to 570° C., more specifically from 530° C. to 570° C., for the nucleation step, followed by at least two crystallization steps selected from the ranges from 620° C. to 680° C., from 800° C. to 820° C. and from 825° C. to 830° C., depending on the desired crystalline phases to be formed and their proportions in relation to each other and to the amorphous phase. The duration for any of these steps typically vary in the range from 30 minutes to 10 hours, also depending on the desired crystalline phases to be formed and their proportions.

It is understood that the process of the present invention can comprise one or more crystallization steps in addition to the first and the second crystallization steps mentioned above, leading to three or more crystallization steps.

Besides their temperature ranges, the individual crystallization steps can also differ in their holding times.

By performing crystallization steps within the above specified temperature ranges, a glass-ceramic material can be achieved comprising different crystalline phases, such as lithium disilicate, lithium metasilicate, lithium phosphate, lithium aluminosilicate as beta-spodumene solid solution, and cristobalite, and that the respective proportions of the crystalline phases can be adjusted to the actual needs.

As will be shown in detail below, it is particularly preferred that the final glass-ceramic material comprises as the two main crystalline phases a lithium disilicate phase and a lithium aluminosilicate phase. As mentioned, the present invention allows for providing various proportions of these phases by adjusting the temperature and the duration of the crystallization steps.

Regarding the co-existence of a lithium disilicate phase and a lithium aluminosilicate phase, desirable new properties can be achieved. In particular, a glass-ceramic body can be achieved having mechanical properties between the properties of lithium aluminosilicate glass-ceramic having excellent thermal properties and relatively moderate mechanical properties (with a flexural strength of 75 to 150 MPa and a fracture toughness $K_{1c}$ of 1 to 2 MPa·m$^{1/2}$) and of lithium disilicate glass-ceramic having a high strength (with a flexural strength of 350 to 400 MPa and a fracture toughness $K_{1c}$ of 2.3 to 2.9 MPa·m$^{1/2}$) and relatively low thermal properties (with a coefficient of thermal expansion of 80 to 120·10$^{-7}$ deg$^{-1}$).

For the particular embodiment specified in the examples below it has for example been shown that the formation of lithium metasilicate and lithium disilicate is favoured at the temperature range from 620° C. to 820° C. and glass-ceramic materials having a flexural strength of 300 to 400 MPa and a fracture toughness $K_{1c}$ of 2.0 to 2.6 MPa·m$^{1/2}$ with a coefficient of thermal expansion of 60 to 90·10$^{-7}$ deg$^{-1}$ can be achieved. At the temperature range from 825° C. to 860° C., the crystallization of lithium aluminosilicate phases is dominant and a glass-ceramic material having a flexural strength of 280 to 330 MPa and a fracture toughness $K_{1c}$ of 2.0 to 2.3 MPa·m$^{1/2}$ with a coefficient of thermal expansion of 40 to 60·10$^{-7}$ deg$^{-1}$ can be achieved.

Also, the chemical resistance of the final glass-ceramic can be adjusted. In this regard, a high proportion of lithium disilicate crystalline phase is generally preferable if a high chemical resistance of the final glass-ceramic material is to be achieved.

According to a particularly preferred embodiment of the present invention, a first region of the glass body is subjected to the first crystallization step and a second region of the glass body different to the first region is subjected to the second crystallization step such that the proportion of the first crystalline phase (e.g. lithium disilicate) is higher in the first region than in the second region and the proportion of the second crystalline phase (e.g. lithium aluminosilicates) is higher in the second region than in the first region.

The term "proportion" of the respective crystalline phase is in the context of the present invention to be understood as volume-% based on the total volume of the final glass-ceramic body.

As for the crystallization steps, embodiments are encompassed in which the first region is exclusively subjected to the first crystallization step and the second region is exclusively subjected to the second crystallization step. In particular if the second crystallization step is at a higher temperature range, it is also thinkable that the second region is also subjected to the first crystallization step before it is subjected to the second crystallization step.

The first temperature range is preferably from 620° C. to 820° C. The second temperature range is preferably starting from 825° C., and is more preferably from 825° to about 1000° C., most preferably from 825° C. to about 860° C.

More particularly, a crystalline phase of $Li_2Si_2O_5$ (lithium disilicate) is predominantly formed at the first region, and a further crystalline phase being selected from the group consisting of $LiAlSi_2O_6$, $LiAlSiO_4$, $LiAlSi_3O_8$, $LiAlSi_4O_{10}$ (lithium aluminosilicate) is predominantly formed at the second region, whereby—according to a particularly preferred embodiment—the proportion of the crystalline phases change from one region to the other in a gradual manner.

This is of particular relevance for preparing a glass-ceramic material to be used for dental restorations, since regions comprising a lithium disilicate crystalline phase generally are translucent resembling enamel whereas regions comprising a lithium aluminosilicate crystalline phase are opaque resembling dentin. By performing a controlled thermal treatment, a glass-ceramic body can thus be obtained comprising inhomogenously distributed crystalline phases attributing to an inhomogenous colour distribution resembling the colour distribution of a natural tooth.

Also with regard to the mechanical properties, the structure of a natural tooth can be accurately mimicked by the inhomogenously distributed crystalline phases, as the lithium disilicate phase imparts a higher strength than the lithium aluminosilicate phase corresponding to the natural situation with the enamel having a higher strength than the dentin.

Also the high chemical resistance of the lithium disilicate glass-ceramic region attributes to its feasibility for an enamel-like region.

In view of the CAD/CAM machining of the glass-ceramic body, adjustment of the formation of different crystalline phases in different regions of the body further allows a favourable distribution of stresses which strengthens the body and makes it less prone to fracture. In particular, a favourable stress distribution is obtained if the crystalline phases change from one region to another in a gradual manner. Regarding e.g. the coefficient of thermal expansion, which is different in a lithium disilicate glass-ceramic region than in a lithium aluminosilicate glass-ceramic region, a smooth transition can thus be achieved. This ultimately leads to a body being well suited for CAD/CAM machining of both single-unit restorations as well as multi-unit bridges. In addition, the distribution of the crystalline phases can be adjusted such that the areas to be machined off the block are preferably predominantly of a softer material than e.g. the areas which will be present in the ultimate restoration.

The process of the present invention is not confined locally to the surface area of the body, but allows the selective and controlled formation of different crystalline phases throughout the body and in particular in the interior of the body remote from the surface. A spatially confined and controlled thermal treatment leading to a selective and controlled crystallization can for example be performed by laser irradiation, as demonstrated by Kawasaki et al. (Journal of Non-Crystalline Solids 325 (2003) 61 to 69), Honma et al. (Applied Physics Letters 83 (2003), 2796 to 2798), Fujiwara et al. (Chem. Glasses 43C (2002) 213), Gupta et al. (Optical Materials 2005) and others. Other methods allowing a focused and spatially limited heating of the basic glass body, using e.g. electromagnetic radiation or susceptors, are also possible. Also, methods using a cooling paste for heat confinement, i.e. by shielding certain areas of the basic glass body from being heated, can likewise be performed.

Although the present invention encompasses also the possibility of forming different crystalline phases in spatially separated regions, the process of the present invention is preferably carried out in a manner such that different crystalline phases changing from one region to another in a gradual manner are formed. This is also of particular relevance concerning the use of the body for a dental restoration as also in a natural tooth the different structural components change in a gradual manner. Also, any stability problems which might arise at an interface of different materials can be avoided.

According to a very straightforward technique, a temperature gradient can be achieved in the basic glass body by appropriately placing the body in a heating furnace in which such a temperature gradient is present, thus leading to a gradual change of the crystalline phase composition along the gradient.

Apart from the process described above, the present invention further relates to a glass composition comprising 65 to 72 wt-% $SiO_2$, at least 10.1 wt-% $Li_2O$ and at least 10.1 wt-% $Al_2O_3$ based on the total weight of the composition. Preferably, the proportion of $Li_2O$ to $Al_2O_3$ is at least 1:1, and more preferably is about 3:2. It is understood that the term "proportion of $Li_2O$ to $Al_2O_3$" means the ratio of the amount of $Li_2O$ to the amount of $Al_2O_3$.

The glass composition is particularly useful for the process described above. Based on this composition, the desirable glass-ceramic material can be prepared in a simple and straightforward manner, as mentioned above. Particularly, a great variety of different crystalline phases may be formed.

Preferably, the glass compositions of the instant invention comprise at most 15 wt-% of $Li_2O$ and/or at most 15 wt-% of $Al_2O_3$.

According to a specific embodiment, the proportion of $Li_2O$ to $Al_2O_3$ is from 1:1 to 1.5:1.

According to a preferred embodiment, the composition further comprises 0 to 2 wt-% $K_2O$, 1 to 4 wt-% $Na_2O$ and 0 to 1.5 wt-% $CeO_2$. In this regard, the present invention also encompasses a composition essentially consisting of 0 to 2 wt-% $K_2O$, 1 to 4 wt-% $Na_2O$ and 0 to 1.5 wt-% $CeO_2$ besides $SiO_2$, $Li_2O$ and $Al_2O_3$.

Depending on the final glass-ceramic body to be achieved, different crystallization agents can be used in the glass composition. Typically, the composition thus further comprises 0 to 1.5 wt-% CaO, 0 to 1.0 wt-% MgO, 0 to 1.5 wt-% $B_2O_3$, 1 to 5 wt-% $P_2O_5$, 0 to 3 wt-% $CaF_2$, 0 to 2.0 wt-% $AlF_3$, 0 to 1.0 wt-% Ag, 0 to 5 wt-% $ZrO_2$ and 0 to 4 wt-% $TiO_2$ based on the total weight of the composition. In this regard, the present invention also encompasses a composition essentially consisting of 0 to 1.5 wt-% CaO, 0 to 1.0 wt-% MgO, 0 to 1.5 wt-% $B_2O_3$, 1 to 5 wt-% $P_2O_5$, 0 to 3 wt-% $CaF_2$, 0 to 2.0 wt-% $AlF_3$, 0 to 1.0 wt-% Ag, 0 to 5 wt-% $ZrO_2$ and 0 to 4 wt-% $TiO_2$ besides $SiO_2$, $Li_2O$ and $Al_2O_3$ and, optionally, $K_2O$, $Na_2O$ and $CeO_2$ in the amounts specified above, whereby preferably the proportion of $Li_2O$ to $Al_2O_3$ is from 1:1 to 1.5:1. A glass composition being devoid of $ZrO_2$ and $TiO_2$ is particularly preferred for achieving a relatively high content of a lithium disilicate crystalline phase, in particular in comparison to lithium aluminosilicate phases.

According to an alternative preferred embodiment, the glass composition, besides $SiO_2$, $Li_2O$ and $Al_2O_3$, comprises 0 to 2 wt-%, preferably 0 to 1 wt-% $K_2O$, at most 4 wt-%, preferably at most 2.5 wt-% $Na_2O$, 0 to 1.5 wt-% CaO, 0 to 1.5 wt-% $CeO_2$, 1 to 5 wt-%, preferably 3 to 5 wt-% $P_2O_5$, 0 to 0.5 wt-%, preferably 0 to 0.1 wt-%, very preferably 0 to 0.05 wt-% $V_2O_5$, 0 to 1 wt-% Ag and 0 to 1 wt-% $ZrO_2$, the composition being devoid of $TiO_2$, $Cu_2O$, BaO, $Sb_2O_3$, $Nb_2O_5$, MgO, $La_2O_3$ and $SnO_2$. It is thereby particularly preferred that the glass composition essentially consists of 0 to 2 wt-%, preferably 0 to 1 wt-% $K_2O$, at most 4 wt-%, preferably at most 2.5 wt-% $Na_2O$, 0 to 1.5 wt-% CaO, 0 to 1.5 wt-% $CeO_2$, 1 to 5 wt-%, preferably 3 to 5 wt-% $P_2O_5$, 0 to 0.5 wt-%, preferably 0 to 0.1 wt-%, very preferably 0 to 0.05 wt-% $V_2O_5$, 0 to 1 wt-%, preferably 0 wt-% Ag and 0 to 1 wt-% $ZrO_2$ besides $SiO_2$, $Li_2O$ and $Al_2O_3$ in the amounts given above, whereby preferably the proportion of $Li_2O$ to $Al_2O_3$ is from 1:1 to 1.5:1. Also in this alternative embodiment, the glass composition is preferably devoid of $ZrO_2$ for achieving a relatively high content of a lithium disilicate crystalline phase, in particular in comparison to lithium aluminosilicate phases.

According to another alternative preferred embodiment, the glass composition comprises 65 to 72 wt-% $SiO_2$, at least 10.1 wt-% $Li_2O$, at least 10.1 wt-% $Al_2O_3$, whereby preferably the proportion of $Li_2O$ to $Al_2O_3$ is from 1:1 to 1.5:1, 1 to 5 wt-%, preferably 3 to 5 wt-% $P_2O_5$, and optionally 0 to 1.5 wt-% $CeO_2$, 0 to 0.1 wt-%, preferably 0 to 0.05 wt-% $V_2O_5$, 0 to 2 wt-%, preferably 0 to 1 wt-% $K_2O$, at most 4 wt-%, preferably at most 2.5 wt-% $Na_2O$, 0 to 1.5 wt-% CaO, 0 to 1 wt-% Ag and 0 to 1 wt-% $ZrO_2$, the composition being devoid of $TiO_2$, $Cu_2O$, BaO, $Sb_2O_3$, $Nb_2O_5$, MgO, $La_2O_3$ and $SnO_2$. It is thereby particularly preferred that the glass composition essentially consists of 65 to 72 wt-% $SiO_2$, at least 10.1 wt-% $Li_2O$, at least 10.1 wt-% $Al_2O_3$, whereby preferably the proportion of $Li_2O$ to $Al_2O_3$ is from 1:1 to 1.5:1, 1 to 5 wt-%, preferably 3 to 5 wt-% $P_2O_5$, and optionally 0 to 1.5 wt-% $CeO_2$, 0 to 0.1 wt-%, preferably 0 to 0.05 wt-% $V_2O_5$, 0 to 2 wt-%, preferably 0 to 1 wt-% $K_2O$, at most 4 wt-%, preferably at most 2.5 wt-% $Na_2O$, 0 to 1.5 wt-% CaO, 0 to 1 wt-% Ag and 0 to 1 wt-% $ZrO_2$. Also in this alternative embodiment, the glass composition is preferably devoid of $ZrO_2$ for achieving a relatively high content of a lithium disilicate crystalline phase, in particular in comparison to lithium aluminosilicate phases.

Typical glass compositions suitable for the purposes of the present invention are as follows:

| Composition I | |
| --- | --- |
| component | amount (wt-%) |
| $SiO_2$ | 67.3 |
| $Li_2O$ | 10.1 |
| $Al_2O_3$ | 10.1 |
| $K_2O$ | 0.5 |
| $Na_2O$ | 2.5 |
| $ZrO_2$ | 3.0 |
| $CeO_2$ | 1.4 |
| $V_2O_5$ | 0.05 |
| CaO | 1.55 |
| $P_2O_5$ | 3.5 |

| Composition II | |
| --- | --- |
| component | amount (wt-%) |
| $SiO_2$ | 68.7 |
| $Li_2O$ | 10.1 |
| $Al_2O_3$ | 10.1 |
| $K_2O$ | 0.5 |
| $Na_2O$ | 2.5 |
| $ZrO_2$ | 0.5 |
| $CeO_2$ | 1.5 |
| $V_2O_5$ | 0.05 |
| CaO | 1.55 |
| $P_2O_5$ | 4.5 |

| Composition III | |
| --- | --- |
| component | amount (wt-%) |
| $SiO_2$ | 68.0 |
| $Li_2O$ | 10.5 |

-continued

Composition III

| component | amount (wt-%) |
|---|---|
| $Al_2O_3$ | 10.5 |
| $K_2O$ | 0.5 |
| $Na_2O$ | 2.5 |
| $ZrO_2$ | 0.5 |
| $CeO_2$ | 1.5 |
| $V_2O_5$ | 0.05 |
| CaO | 1.45 |
| $P_2O_5$ | 4.5 |

Composition IV

| component | amount (wt-%) |
|---|---|
| $SiO_2$ | 69.5 |
| $Li_2O$ | 10.5 |
| $Al_2O_3$ | 10.5 |
| $K_2O$ | 0.5 |
| $Na_2O$ | 1.0 |
| $ZrO_2$ | 0.5 |
| $CeO_2$ | 1.5 |
| $V_2O_5$ | 0.05 |
| CaO | 1.45 |
| $P_2O_5$ | 4.5 |

Composition V

| component | amount (wt-%) |
|---|---|
| $SiO_2$ | 69.5 |
| $Li_2O$ | 15.0 |
| $Al_2O_3$ | 10.5 |
| $CeO_2$ | 1.45 |
| $V_2O_5$ | 0.05 |
| $P_2O_5$ | 3.5 |

All preferred features of the glass composition mentioned above, and in particular all specific glass compositions, are analogously preferred with regard to the described process for preparing a glass-ceramic body. They are likewise preferred with regard to the glass-ceramic body itself and to its use for a dental restoration, described below.

According to a further aspect, the present invention further relates a glass-ceramic body comprising at least two crystalline phases selected from the group consisting of $Li_2SiO_3$, $Li_2Si_2O_5$, $LiAlSi_2O_6$, $LiAlSiO_4$, $LiAlSi_3O_8$, $LiAlSi_4O_{10}$ and $Li_3PO_4$.

Preferably, the glass-ceramic body comprises five crystalline phases selected from the group consisting of $Li_2SiO_3$, $Li_2Si_2O_5$, $LiAlSi_2O_6$, $LiAlSiO_4$, $LiAlSi_3O_8$, $LiAlSi_4O_{10}$ and $Li_3PO_4$, thus allowing an almost unlimited adjustment of properties of the body by suitably choosing the crystalline phases and the proportion in which they are present.

According to a particularly preferred embodiment, the glass-ceramic body comprises
a) a first crystalline phase of $Li_2Si_2O_5$ (lithium disilicate) and
b) a second crystalline phase selected from the group consisting of $LiAlSi_2O_6$, $LiAlSiO_4$, $LiAlSi_3O_8$ and $LiAlSi_4O_{10}$.

The second crystalline phase is thus a lithium aluminosilicate; among the group mentioned, $LiAlSi_2O_6$ and $LiAlSi_3O_8$ are preferred.

A particularly preferred combination is $LiAlSi_2O_6$, $LiAlSi_3O_8$ and $Li_2Si_2O_5$ further comprising $Li_3PO_4$.

As mentioned above, the type of crystalline phase as well as its proportion in the glass-ceramic body of the present invention can be controlled by adjusting the temperature profile. For example, a two phase material having a ratio of lithium aluminosilicate and lithium disilicate ranging from about 30:70 to about 60:40 can be achieved.

As also mentioned above, it is preferred that the glass-ceramic body comprises a first region and a second region different to the first region, wherein in the first region the proportion of the first crystalline phase is higher than in the second region and in the second region the proportion of the second crystalline phase is higher than in the first region, thus allowing the inhomogeneous structure of e.g. a natural tooth to be mimicked.

This includes embodiments comprising in the first and the second region at least one further crystalline phase in addition to the first crystalline phase and the second crystalline phase, respectively. In particular, it encompasses embodiments comprising in the first region also the second crystallization phase to a lower proportion than the first crystalline phase and/or in the second region also the first crystalline phase to a lower proportion than the second crystalline phase.

In this regard, it is further preferred that the first crystalline phase and the second crystalline phase change gradually from region to region. This encompasses embodiments in which the first crystalline phase decreases gradually with an increase in the second crystalline phase and vice versa, i.e. without a purely amorphous phase disposed between the regions, as well as embodiments in which the first crystalline phase decreases in direction to the second region and the second crystalline phase decreases in direction to the first region with a purely amorphous phase disposed between the regions.

According to a particularly preferred embodiment, the glass-ceramic body is in the form of a dental restoration having an enamel area and a dentin area corresponding to the respective areas of a natural tooth, with the first region being arranged in the enamel area and the second region being arranged in the dentin area.

Since with regard to colour and mechanical properties, the lithium disilicate phase resembles the enamel, whereas the lithium aluminosilicate phase resembles the dentin of a natural tooth, superior restorations can be achieved by suitable choosing the distribution of these phases. Also, due to the lithium aluminosilicate being opaque, a metal abutment or implant can be shielded from shining through the restoration by suitably arranging the lithium aluminosilicate phase within the body.

According to a further aspect, the present invention thus also relates to the use of the glass-ceramic body for a dental restoration. Specifically, the present invention relates to the use of the glass-ceramic body for inlays, onlays, veneers, crowns and bridges up to multi-unit bridges.

In particular, this use also encompasses the use of the glass-ceramic body as a blank for a CAD/CAM machining process to prepare a dental restoration. Likewise, the basic glass body can be subjected to the CAD/CAM machining process prior to the thermal treatment involving the crystallization steps, since the change in volume of the body accompanied by the formation of the crystalline phases is insignificant.

It is understood that the glass-ceramic body of the present invention can likewise be used for other technological areas, in particular areas in which a good heat shock resistance and/or chemical resistance of the material is of relevance.

Specifically the glass-ceramic body can be used for cooktops (plates and other elements), cookware and/or bakeware.

A particularly interesting use is in the field of (chemical) laboratory equipment, which in general is both subjected to high temperatures as well as to harsh chemical conditions.

Other areas include apparatuses for the generation, the distribution and the use of energy, in particular power plants. A specific area of interest is the use in solar heat collection elements comprising a glass-ceramic central tube.

BRIEF DESCRIPTION OF THE DRAWINGS

The present invention is further illustrated by way of the following examples in combination with the attached figures, of which

DETAILED DESCRIPTION

Examples

The following experiments are based on the following (raw) glass composition:

| component | amount (wt-%) |
|---|---|
| $SiO_2$ | 66.5 |
| $Li_2O$ | 10.5 |
| $Al_2O_3$ | 10.5 |
| $K_2O$ | 0.45 |
| $Na_2O$ | 4.0 |
| $ZrO_2$ | 3.0 |
| $CeO_2$ | 1.5 |
| $V_2O_5$ | 0.05 |
| $P_2O_5$ | 3.5 |

Differential Scanning Calorimetry (DSC) and Differential Thermal Analysis (DTA) of the composition has shown three peaks, one at about 655° C., one at about 812° C. and one at about 826° C., indicative of three crystallization steps.

Based on these findings, a first sample of the glass-composition has—after a nucleation step at 550° C. for three hours—been subjected to a crystallisation step at 660° C. for three hours (crystallisation step I). A second and a third sample were subjected to a crystallisation step at 815° C. for three hours (crystallisation step II) following crystallisation step I and a crystallisation step at 830° C. for three hours (crystallisation step III) following crystallisation step I.

X-ray diffraction (XRD) analysis has revealed a formation of $Li_2SiO_3$ (lithium metasilicate) and lithium aluminosilicate (LAS) at crystallization step I, and a formation of $Li_2Si_2O_5$ (lithium disilicate) and lithium aluminosilicate at crystallization step II and crystallization step III, with an increased content of lithium aluminosilicate (as spodumen) and a decreased content of lithium disilicate formed in crystallization step III in comparison to crystallization step II.

The content of different phases in the final glass-ceramic in relation to different heat treatments has further been determined. In this regard, the raw glass composition has—after a nucleation step at 550° C. for three hours and a first crystallization step at 660° C. for three hours—been subjected to a second crystallization step at a further temperature for three hours, specifically at a temperature of 760° C. (sample 1), 790° C. (sample 2), 820° C. (sample 3) and 850° C. (sample 4). The results are shown in FIG. 1.

Figure 1:
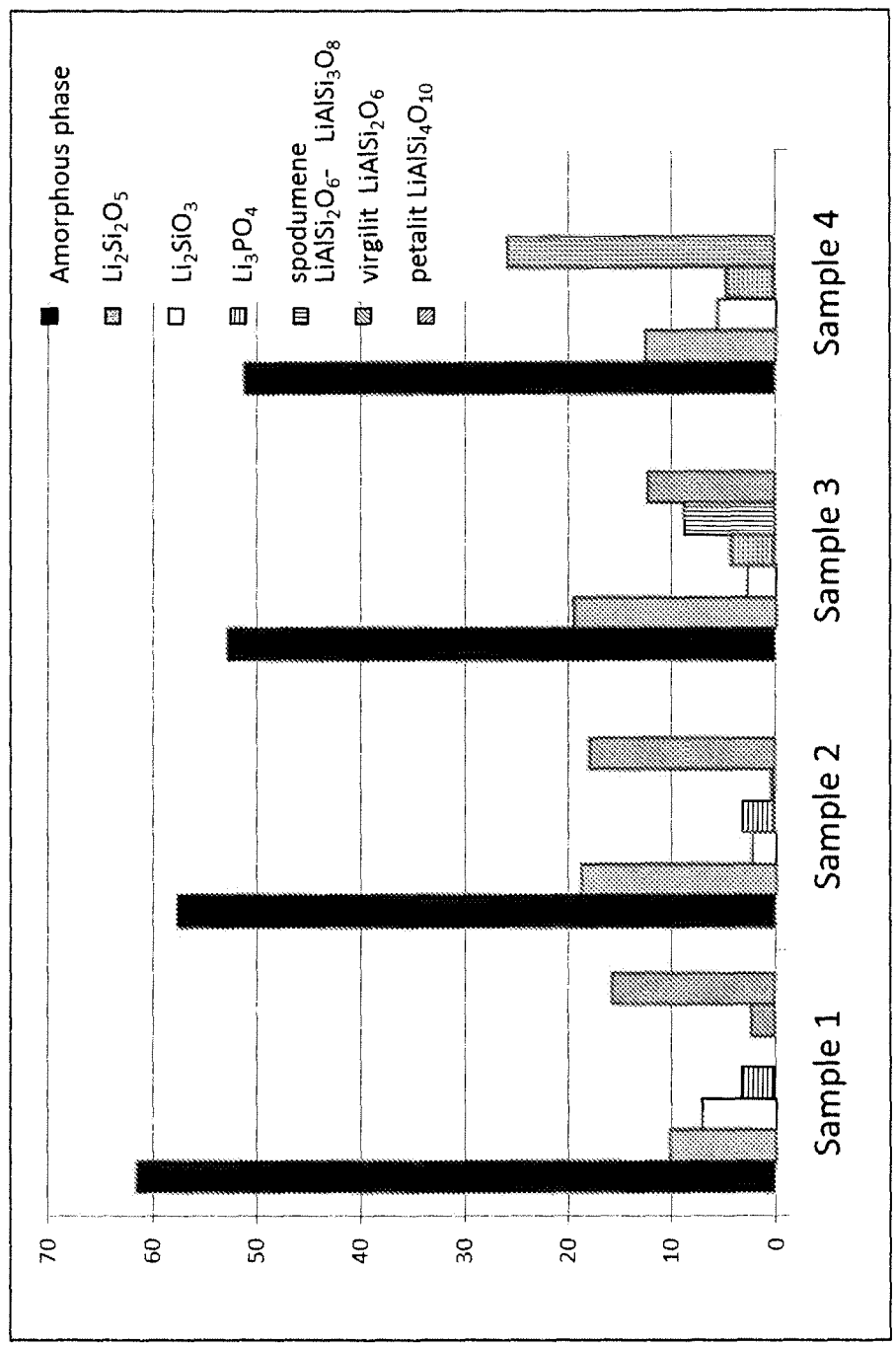
FIG. 1 shows a graphical representation of the proportion of different phases (in volume-%) in a glass-ceramic material obtained by subjecting the glass composition according to the present invention to different temperature treatments.

As shown in FIG. 1, the content of the different phases in the final glass-ceramic material is highly dependent on the temperature of the second crystallization step. For example, a decrease in the amorphous phase with an increase in the temperature of the second crystallization step has been detected. For the lithium disilicate phase, the highest content has been detected in samples 2 and 3, for which the second crystallization step has been at a temperature of 790° C. and 820° C., respectively. Lithium aluminosilicate is in sample 1 predominantly present as petalite and in sample 2 almost exclusively present as virgilite. In sample 3, it is present both as virgilite and spodumene, whereas in sample 4 it is exclusively present as spodumene.

The results given in FIG. 1 both illustrate that several crystalline phases can be formed in one and the same glass-ceramic material and that the type of crystalline phase and its content can be controlled by adjusting the temperature treatment.

It has been shown that different crystalline phases resulting in different mechanical and optical properties can be achieved in one and the same glass-ceramic body by applying a temperature gradient for the heat treatment. For example, a temperature gradient can be provided in a furnace in which the temperature gradually decreases with increasing distance from the heating source of the furnace (e.g. located in the middle of the furnace). By appropriately placing the respective body into the furnace, the temperature gradient is established in the material, leading to crystalline phases gradually changing from one region to another.

Specifically, it has been shown that by subjecting the glass composition of the present example to a temperature gradient starting at about 550° C., opalescence starts to form at about 570° C. At about 620° C., a violet shade in reflectance light and a yellow shade in transmittance light can be detected, and at about 670° C. opalescence is marked. An opaque material is achieved starting at about 700° C.

By means of the glass composition of the present example it could, thus, be shown that the invention not only allows for the formation of different crystalline phases in different regions of one and the same body, but also for a gradual change of the crystalline phases from one region to another.

Figure 2:
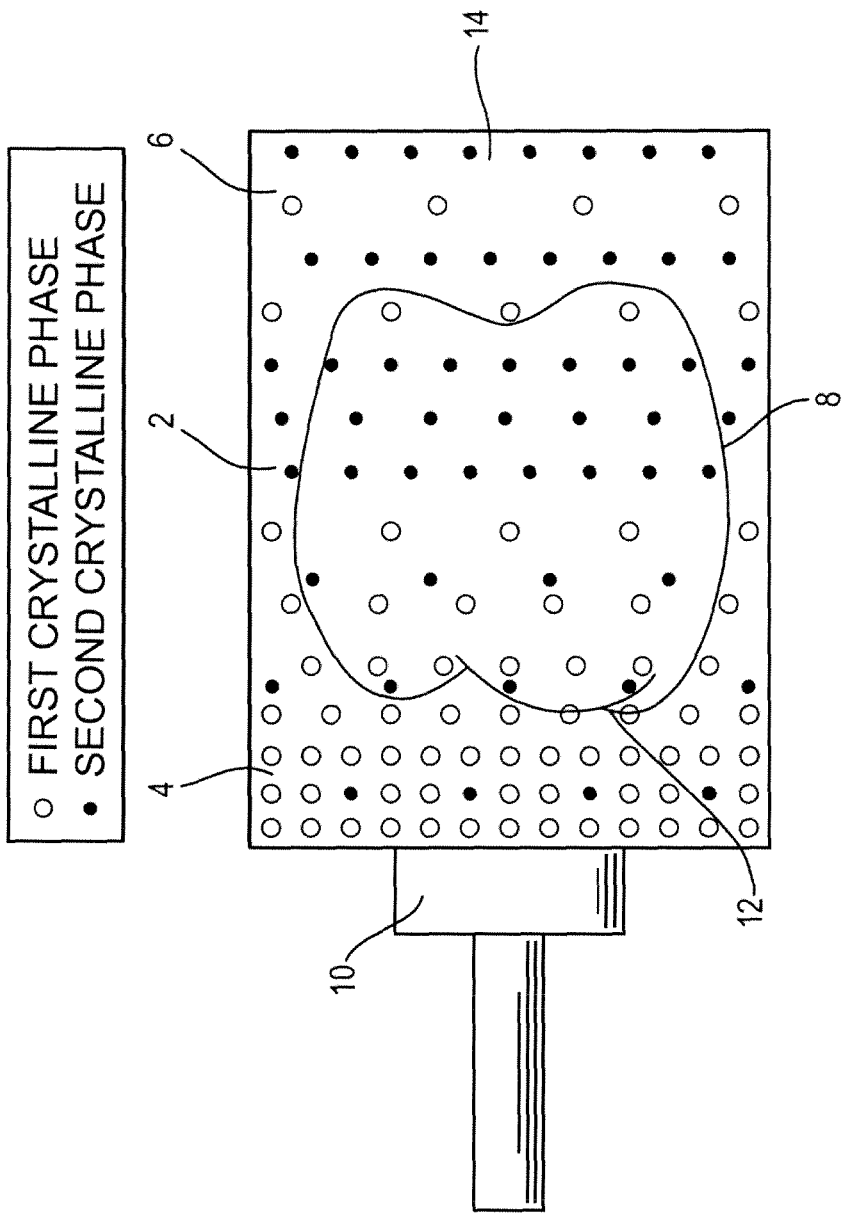
FIG. 2 shows a purely schematic representation of a preferred glass-ceramic body according to the present invention to be subjected to a CAD/CAM process for preparing a dental restoration, as well as a holder for holding the body.

As schematically shown in FIG. 2, the glass-ceramic body 2 of the present invention comprises a first region 4 comprising a high proportion of a first crystalline phase and a second region 6 comprising a high proportion of a second crystalline phase. Depending on the local properties to be achieved in the final restorations 8, the portions to be removed are determined and the body is arranged correspondingly. A holder 10 safeguards that the body is kept in place during the computer-aided machining.

Given the distribution of the crystalline phases, a final restoration can be achieved, the load bearing surfaces 12 having a higher toughness than e.g. the bulk area 14 of the body 2 to be removed. Thus, a dental restoration with high toughness in e.g. the pontics, the cusp supporting areas or the edges can be achieved in a relatively easy manner without undue wear of the machining tools.

The invention claimed is:

1. A process for preparing a glass-ceramic body comprising the steps of providing a basic glass body and subjecting the basic glass body to a thermal treatment whereby a crystalline phase embedded in a glass matrix is formed, wherein the basic glass body is made of a composition comprising 65 to 72 wt-% $SiO_2$, at least 10.1 wt-% $Li_2O$ and at least 10.1 wt-% $Al_2O_3$ based on the total weight of the composition, the proportion of $Li_2O$ to $Al_2O_3$ being from 1:1 to 1.5:1, and the thermal treatment involves a nucleation step followed by a first crystallization step at a first temperature range and a second crystallization step at a second temperature range different from the first temperature range, wherein at least two different crystalline phases are formed.

2. The process for preparing a glass-ceramic body according to claim 1, wherein a first region of the glass body is subjected to the first crystallization step and a second region of the glass body different to the first region is subjected to the second crystallization step such that the proportion of the first crystalline phase is higher in the first region than in the second region and the proportion of the second crystalline phase is higher in the second region than in the first region.

3. The process according to claim 2, wherein the regions are heated to the respective temperature ranges by means of laser irradiation, electromagnetic radiation and/or susceptors.

4. The process according to claim 1, wherein the first temperature range is from 620 to 820° C. and the second temperature range is starting from 825° C.

5. A glass composition comprising:
65 to 72 wt-% $SiO_2$,
at least 10.1 wt-% $Li_2O$,
at least 10.1 wt-% $Al_2O_3$,
0 to 2 wt-% $K_2O$,
1 to 4 wt-% $Na_2O$,
0 to 1.5 wt-% CaO,
0 to 1.0 wt-% MgO,
0 to 1.5 wt-% $B_2O_3$,
0 to 1.5 wt-% $CeO_2$,
1 to 5 wt-% $P_2O_5$,
0 to 3 wt-% $CaF_2$,
0 to 2.0 wt-% $AlF_3$,
0 to 1.0 wt-% Ag,
0 to 5 wt-% $ZrO_2$, and
0 to 4 wt-% $TiO_2$ based on a total weight of the composition, the proportion of $Li_2O$ to $Al_2O_3$ being from 1:1 to 1.5:1.

6. The glass composition according to claim 5, comprising at most 15 wt-% of $Li_2O$ and/or at most 15 wt-% of $Al_2O_3$.

7. A glass-ceramic body comprising:
a) a first crystalline phase of $Li_2Si_2O_5$, and
b) a second crystalline phase selected from the group consisting of $LiAlSi_2O_6$, $LiAlSiO_4$, $LiAlSi_3O_8$ and $LiAlSi_4O_{10}$;
the glass-ceramic body comprising a first region and a second region different from the first region;
wherein:
a proportion of the first crystalline phase is higher in the first region than in the second region; and
a proportion of the second crystalline phase is higher in the second region than in the first region.

8. The glass-ceramic body according to claim 7, wherein:
the proportion of the first crystalline phase decreases and the proportion of the second crystalline phase increases in a direction from the first region to the second region; or
the proportion of the first crystalline phase decreases in a direction from the first region to the second region and the proportion of the second crystalline phase decreases in a direction from the second region to the first region with an amorphous phase disposed between the first region and the second region.

9. The glass-ceramic according to claim 7, the glass-ceramic body being in the form of a dental restoration having an enamel area and a dentin area corresponding to the respective areas of a natural tooth, with the first region being arranged in the enamel area and the second region being arranged in the dentin area.

10. A method of forming a dental restoration comprising forming a dental restoration from the glass-ceramic body of claim 7.

11. The glass-ceramic body according to claim 8, the glass-ceramic body being in the form of a dental restoration having an enamel area and a dentin area corresponding to the respective areas of a natural tooth, with the first region being arranged in the enamel area and the second region being arranged in the dentin area.

* * * * *